United States Patent [19]

Thenappan et al.

[11] Patent Number: 5,629,458
[45] Date of Patent: May 13, 1997

[54] PROCESS FOR THE PREPARATION OF 2 2 2 TRIFLUOROETHANOL

[75] Inventors: Alagappan Thenappan, Cheektowaga; Michael Van Der Puy, Amherst; Richard Eibeck, Orchard Park, all of N.Y.

[73] Assignee: AlliedSignal Inc., Morris County, N.J.

[21] Appl. No.: 686,742

[22] Filed: Jul. 26, 1996

[51] Int. Cl.$^6$ .................................................. C07C 29/70
[52] U.S. Cl. ........................................ 568/842; 570/134
[58] Field of Search ............................ 568/842; 570/134

[56] References Cited

U.S. PATENT DOCUMENTS

| | | | |
|---|---|---|---|
| 4,189,615 | 2/1980 | Childs | 568/842 |
| 4,434,297 | 2/1984 | Astrologes et al. | 560/236 |
| 4,542,245 | 9/1985 | Lecloux et al. | 568/842 |
| 4,590,310 | 5/1986 | Townsend et al. | 568/842 |
| 4,647,786 | 3/1987 | Cheminal et al. | 568/842 |

FOREIGN PATENT DOCUMENTS

| | | |
|---|---|---|
| 2544712 | 4/1983 | France . |
| 04005247 | 1/1992 | Japan . |
| 98360 | 8/1978 | Poland . |

OTHER PUBLICATIONS

W.T. Miller, Jr. and A.L. Dittman. "The Mechanism of Fluorination. I." *J. Amer. Chem. Soc.*, Jun. 20, 1956, p. 2793.

F.J. Dillemuth et al. "Reaction of Ozone with 1,1–difluoroethane and 1,1,1–Trifluoroethane" *J. Phys. Chem.*, vol. 80, No. 6 (1976) p. 571.

A.L. Henne and M.W. Renoll. "Fluoroethanes and Fluoroethylenes. V." *J. Am. Chem. Soc.* (Jun., 1936) p. 889.

D.R. Allen. "Preparation of Trifluoroacetic Acid" *J. Org. Chem.* vol. 26, (Mar., 1961) p. 923.

*Primary Examiner*—Gary Geist
*Assistant Examiner*—Sreeni Padmanabhan
*Attorney, Agent, or Firm*—Jay P. Friedenson

[57] ABSTRACT

A vapor phase process for producing a fluorinated alcohol, such as 2,2,2-trifluoroethanol via oxidation of an hydrofluorocarbon, such as 1,1,1-trifluoroethane, with an oxidizing agent and elemental fluorine.

19 Claims, No Drawings

PROCESS FOR THE PREPARATION OF 2 2 2 TRIFLUOROETHANOL

FIELD OF THE INVENTION

This invention relates to a vapor phase process for the preparation of 2,2,2-trifluoroethanol. Specifically, the present invention provides a method for preparing 2,2,2-trifluoroethanol via oxidation of 1,1,1-trifluoroethane with an oxidizing agent and elemental fluorine.

BACKGROUND OF THE INVENTION

The major application of 2,2,2-trifluoroethanol (i.e., $CF_3CH_2OH$ or TFE) is in the pharmaceutical industry where it is used as a key raw material for the production of inhalation anesthetics isoflurane and desflurane. Additional applications of TFE include: as a solvent and intermediate in chemical synthesis, as a working fluid in heat absorption pumps and transformers and in energy recovery.

There are three general methods to prepare TFE in the literature each having certain limitations. In the first method, reaction of 1-chloro-2,2,2-trifluoroethane (i.e., $CF_3CH_2Cl$ or HCFC-133a) with an alkali metal salt of a carboxylic acid followed by aqueous basic hydrolysis to form TFE (U.S. Pat. Nos. 4,434,297 and 4,590,310) requires anhydrous reaction conditions and a solvent. In addition, separation of the trifluoroethanol from the aqueous reaction mixture during hydrolysis is difficult.

The second method involves a combination of oxidation-reduction sequence where a chlorine containing hydrochlorofluorocarbon such as 133a or 1,1-dichloro-2,2,2-trifluoroethane (i.e., $CF_3CHCl_2$ or HCFC-123) is initially oxidized to trifluoroacetic acid (i.e., TFA) or one of its derivatives followed by catalytic reduction of the acid or its derivatives to trifluoroethanol. The reduction of TFA (French Patent No. 2,544,712) with a precious metal catalyst requires initial preparation of the acid. In the reduction of trifluoroacetyl chloride (i.e., TFAC), separation of the co-product hydrogen chloride from the starting TFAC is difficult. Reduction of esters of trifluoroacetic acid with alkali metal borohydride and an alcohol or water produces several azeotropes (U.S. Pat. No. 4,189,615) which are difficult to separate. Hydrogenolysis of the trifluoroacetaldehyde (i.e., fluoral) or one of its derivatives requires the initial preparation of the aldehyde by an oxidation procedure (U.S. Pat. No. 4,647,706). In general, reduced catalytic activity over time, difficult separation of the product from co-products and the necessity to prepare the initial starting material by an oxidation procedure followed by reduction to give the alcohol make this approach economically less attractive.

Catalytic oxidation process to prepare TFE from 1,1-difluoroethylene and oxygen (U.S. Pat. No. 4,542,245) requires expensive silver oxide catalyst and the propensity of 1,1-difluoroethylene to polymerize to form varying quantities of coke during oxidation reduces the catalyst life time.

Preparation of TFE from 1,1,1-trifluoroethane (i.e., $CF_3CH_3$ or HFC-143a) has several advantages over other methods. The starting material, HFC-143a can be readily prepared in high yield from 1,1,1-trichloroethane (methyl chloroform or $CH_3CCl_3$ or HCC-140) by a literature procedure [Henne, et al., in *J. Am. Chem. Soc.*, 1936, p. 889] and the process is amenable to commercial scale-up. Oxidation of HFC-143a to TFE does not require any catalyst and the by-product produced is water. The process can also be operated continuously. The present invention describes a process to prepare TFE which can be economically advantageous and ecologically superior to existing processes.

HFC-143a has an estimated life time of about 50 years indicating a slow reaction with hydroxyl radicals. Bromination of HFC-143a with elemental bromine [Japanese Patent No. 4005247] to form 1-bromo-2,2,2-trifluoroethane (i.e., $CF_3CH_2Br$) requires harsh reaction conditions such as 550° C.–800° C. HFC-143a is chlorinated with elemental chlorine under ultraviolet irradiation at 220° C.–230° C. to form 1,1,1-trichloro-2,2,2-trifluoroethane [Polish Patent 98360]. TFA has been prepared in a 50% conversion by the direct oxidation of HFC-143a with air and water vapor in a 15000 voltage electric discharge [Allen, D. R., *J. Org. Chem.*, 26, 1961, p 923]. Treatment of HFC-143a with ozone at 34° C.–86° C. cleaves the carbon-carbon bond of the starting material to form carbon dioxide, carbonylfluoride, formic acid and water [Dillemuth, F. J. et al., *J. Phys. Chem.* 80, 1976, p 571].

Elemental fluorine is unique and different from other halogens in that fluorine-fluorine bond energy is relatively low and carbon-fluorine and hydrogen-fluorine bond energies are very high. These favorable energy differences facilitate the use of elemental fluorine as an initiator in oxidation and halogenation reactions. For example, Miller and co-workers [*J. Amer. Chem. Soc.*, 1956, p 2793] have accumulated enough evidence to indicate the role of fluorine as an initiator in the oxidation of trichloroethylene and tetrachloroethylene. Oxidation of fluorine containing hydrofluorocarbons and hydrochlorofluorocarbons with elemental fluorine as the initiator is not known in the art. In preparing the titled compound, HFC-143a is reacted with air and fluorine in a fluidized bed reactor and the reaction yields the desired TFE in good conversion and selectivity. The fluorine initiated oxidation of HFC-143a to TFE provides a method which is cleaner and cheaper than the existing methods.

SUMMARY OF THE INVENTION

The present invention provides a vapor phase process for the preparation of 2,2,2-trifluoroethanol by oxidation of 1,1,1-trifluoroethane. The process includes of contacting 1,1,1-trifluoroethane with air and fluorine at temperatures ranging from about 50° C. to about 300° C.

DETAILED DESCRIPTION OF THE INVENTION

The present invention provides a process for preparing 2,2,2-trifluoroethanol by the gas phase oxidation of 1,1,1-trifluoroethane with air in the presence of fluorine as the initiator. The process comprises of contacting HFC-143a with fluorine and an oxidizing agent in a fluidized bed reactor in the presence of a particulate phase at temperatures ranging from 50° C.–300° C.

The reactor used in the oxidation process, according to the present invention, is any suitable reactor known in the art, including any simple tubular reactor constructed of a metal resistant to attack by reactants. Preferably the reactor is constructed with either stainless steel or copper, with the most preferred metal being stainless steel. Since reactions involving elemental fluorine are highly exothermic, the reactor is usually packed with a material such as alumina, copper metal turnings, or the like generally known in the art, to provide favorable mixing of the gas streams, good dissipation of heat, and an active surface for the heterogeneous reactions. Preferably the reactor is packed with alumina or copper, with the most preferred packing being alumina. The size of the alumina particulate phase ranges from 120 to 320 mesh with preferred particle size being 180 to 220 mesh. The packing materials used for the oxidation process are commercially available.

The hydrofluorocarbons to be oxidized according to the present invention have a general formula: $[F(CF_2)n] CH_3$, wherein n=1–5. Examples of such hydrofluorocarbons include: $CF_3CH_3$, $CF_3CF_2CH_3$, $CF_3CF_2CF_2CH_3$, $CF_3CF_2CF_2CF_2CH_3$ and $CF_3CF_2CF_2CF_2CF_2CH_3$. The most preferred hydrofluorocarbon for the oxidation is 1,1,1-trifluoroethane.

The products resulting from the oxidation according to the present invention can have a general formula: $[F(CF_2)n] CH_2OH$, wherein n=1–5. Examples of such products include: $CF_3CH_2OH$, $CF_3CF_2CH_2OH$. $CF_3CF_2CF_2CH_2OH$, $CF_3CF_2CF_2CF_2CH_2OH$ and $CF_3CF_2CF_2CF_2CF_2CH_2OH$. The most preferred product from the oxidation is 2,2,2-trifluoroethanol.

Hydrofluorocarbons $CF_3CH_3$ and $CF_3CF_2CH_3$ are commercially available and can also be prepared by any of the processes generally known in the art. For example, $CF_3CH_3$ (HFC-143a) is prepared by the reaction of methyl chloroform, $CH_3CCl_3$, with HF in the presence of antimony catalyst according to the procedure described by Henne, et al., in *J. Am. Chem. Soc.*, 1936, p. 889.

Elemental fluorine gas used in the process is commercially available and the gas is used without any additional purification. Fluorine is usually diluted with a carrier gas to reduce the heat generated in the oxidation process and to reduce the amount of unwanted by-products as well as to adjust the overall residence time of the substrate to be oxidized in the reactor by varying the total gas flow rate. Suitable carrier gases include nitrogen, helium, argon and air. The preferred carrier gases are air and nitrogen, with the most preferred carrier gas being air. Dilution of fluorine with the carrier gas is accomplished by mixing pure fluorine gas with the carrier gas in a concentration required to carry out the oxidation. The gases are allowed to mix in a tee connection and the gases entering the tee connection are measured with flow meters or rotometers of the type well known in the art.

The oxidizing agent useful in the present invention is selected from air, molecular oxygen, and mixtures of nitrogen and oxygen. Preferably the oxidizing agent is either air or mixtures of nitrogen and oxygen, with the most preferred oxidizing agent being air. The oxidizing agents useful for the present invention are commercially available.

The hydrofluorocarbons used in the present invention are either gases or liquids. For liquid hydrofluorocarbons, an inert carrier gas such as nitrogen is used to carry it into the vapor phase by purging the substrate container with the carrier gas.

The oxidation process according to the present invention may be carried out either as a batch or a continuous process. However, for large scale production, the process is conducted preferably in a continuous flow system by passing vapors of carrier gas, fluorine and substrate through a tubular reactor containing the particulate phase.

The oxidation process for the present invention is preferably conducted in the temperature range of about 50° C. to about 300° C. At lower end of the temperature range, the conversion of the starting material is very low and at higher temperatures the amount of by-products increase and the selectivity is diminished. More preferably, the temperature ranges from 150° C.–250° C. and most preferably from 175° C.–225° C. Pressure is not critical for the present invention and it is most convenient to operate the oxidation process at approximately atmospheric pressure with the only pressure above atmospheric being due to back pressure of the system. Useful residence time ranges from about 2 seconds to 100 seconds, preferably from 30–60 seconds. Residence times may be adjusted by changing the volume of the particulate phase, the reaction temperature or the total gas flow rates.

Since the role of fluorine gas is to initiate the reaction, the molar ratio of fluorine to hydrofluorocarbon should be kept at minimum in order to limit the amount of unwanted by-products. The molar ratio of $F_2$/hydrocarbon ranges from 0.01 to 3.0 and preferably the ratio is from 0.01 to 0.5.

Based on reaction stoichiometry, the required ratio of oxygen present in the oxidizing agent to hydrofluorocarbon is 1 and preferably the concentration of the oxygen be kept high to increase the conversion of the hydrofluorocarbon. The most preferred ratio of oxygen to hydrofluorocarbon ranges from 2 to 10.

The oxidation process for the present invention is preferably operated in such a way that either the fluorine conversion is high or unreacted fluorine is returned to the reactor. Similarly the process is operated in such a way that unused oxidizing agent is returned to the reactor.

The resulting oxidized compounds may be separated from the product stream via any known separation or purification method known in the art such as distillation.

EXAMPLES

The following examples serve to illustrate the invention, but are not intended to limit the scope of the invention.

Example 1

The fluidized bed reactor consisted of a vertical stainless steel pipe (2'×2" ID) which was threaded at both the ends to accept caps. A 20 micron porous disc was used at the bottom to retain the particulate phase and to distribute the entering gaseous materials. A ¼" stainless steel tube fitted at the end with a porous frit of 15 micron pores was used to introduce the organic materials. Fluorine and air were introduced through a common ¼" pipe from the bottom. The reactor was initially filled to a depth of 8" (400 ml) with 180 mesh alumina and heated with the air flow. After thermal equilibrium was reached, fluorine was introduced and finally organic was fed from the top. Reactor temperatures were monitored using thermocouples near the reaction and sample exiting zones. Fluorine flow rate to the reactor was measured with a Teledyne Hastings-Raydist, Model ST-M mass flow meter and controlled with a needle valve. Matheson rotometer and flow meters were used to measure the air and organic flow rates. Gases exiting the reactor from the top were directed through a stainless steel tube (1'×1" ID) packed with anhydrous sodium fluoride to trap HF. The HF-free vapors were then passed into a product trap consisting of a one-liter stainless steel cylinder cooled to −78° C. using dry ice/isopropyl alcohol mixture. Uncondensed gases exiting the product trap were passed through an aqueous potassium hydroxide solution. At the conclusion of the run, the fluorine and organic flows were shut off and the stainless steel cylinder containing the products was disconnected and its contents were analyzed by gas chromatography, GC-MS and NMR. The GC analysis was performed on a Hewlett-Packard Series II 5890 Gas Chromatograph coupled with a 3396 integrator.

The fluidized bed reactor was purged with air at the rate of 400 cc/minute and heated to 145° C. When the temperature of the reactor stabilized, fluorine was introduced at a flow rate of 40 cc/minute. After the initial exotherm subsided, HFC-143a was introduced at the flow rate of 15.3 g/h. While feeding 20.4 g (243 mmoles) of HFC-143a in 1 h 20 minutes, two gas samples were collected at the beginning (entry no. 1) and end (entry no. 2) of the oxidation and analyzed by GC and $^{19}F$ NMR. The resulting data and reaction conditions associated with this example are presented in Table I. $^{19}F$ NMR[CDCl$_3$, CFCl$_3$ int.]: -77.8 ppm (m, due to C$F_3$CH$_2$F, HFC-134a) and -78.0 ppm(t, C$F_3$CH$_2$OH).

Examples 2-4

Using the reactor previously described and repeating the procedure illustrated in Example 1, a series of three additional fluorine initiated oxidations of HFC-143a were performed with different F$_2$/143a molar ratios at 217° C.–226° C. (entry nos. 3–5, Table I). A total of 121.8 g of HFC-143a (1.45 moles) was passed through the reactor in 2 hours. These specific runs were intended to demonstrate the use of fluorine as an initiator and not a substrate in the oxidation of 143a to trifluoroethanol. Thus after performing run no.3, the F$_2$/143a molar ratio was reduced by 50% and oxidation was repeated (entry no. 4). Similarly for the next run (entry no. 5), the F$_2$/143a was reduced further by another 50% and oxidation was repeated. The resulting data and reaction conditions associated with these examples are summarized in Table I.

7. A process for producing a fluorinated alcohol in accordance with claim 1, wherein said process is performed in a reactor packed with an alumina having a particulate phase ranging from 120 to 320 mesh.

8. A process for producing a fluorinated alcohol in accordance with claim 1, wherein said process is performed in a reactor packed with of an alumina material having a particulate phase ranging from 180 to 220 mesh.

9. A process for producing a fluorinated alcohol in accordance with claim 1, wherein said fluorine and said oxidizing agent is reacted with said hydrofluorocarbon in a vapor phase.

10. A process for producing a fluorinated alcohol in accordance with claim 1, wherein said process is conducted at temperatures from about 50° C. to about 300° C.

11. A process for producing a fluorinated alcohol in accordance with claim 1, wherein said process has a residence time ranging from 2 seconds to 100 seconds.

12. A process for producing a fluorinated alcohol in accordance with claim 1, wherein a molar ratio of said fluorine to said hydrofluorocarbon ranges from 0.01 to 3.0.

13. A process for producing a fluorinated alcohol in accordance with claim 1, wherein a molar ratio of said oxygen to said hydrofluorocarbon ranges from 2.0 to 10.0.

14. A vapor phase process for producing a fluorinated alcohol in accordance with claim 1, wherein said hydrof-

TABLE 1

| No. | Temperature (C.) Reaction zone | Temperature (C.) Exit zone | Molar ratio F$_2$/143a | Flow Rates (CC/min) Air | Flow Rates (CC/min) F$_2$ | Flow Rates (CC/min) 143a | Conv. 143a (%) | GC Yield (area %) 143a | GC Yield (area %) TFE | GC Yield (area %) HFC-134a | Other pdts. |
|---|---|---|---|---|---|---|---|---|---|---|---|
| 1 | 143 | 148 | 0.54 | 403 | 40.2 | 35 | 1.2 | 98.8 | 0.5 | 0.3 | 0.4 |
| 2 | 190 | 151 | 0.54 | 412 | 40.2 | 35 | 9.0 | 91.1 | 5.1 | 1.3 | 2.5 |
| 3 | 217 | 142 | 0.14 | 402 | 40.2 | 35 | 6.3 | 93.7 | 2.4 | traces | 3.9 |
| 4 | 226 | 144 | 0.07 | 405 | 20.1 | 38 | 14.6 | 85.4 | 9.5 | traces | 5.1 |
| 5 | 220 | 138 | 0.03 | 411 | 10.0 | 35 | 18.1 | 81.9 | 12.8 | traces | 5.3 |

What is claimed is:

1. A process for producing a fluorinated alcohol, comprising:

(a) reacting an hydrofluorocarbon with an oxidizing agent and fluorine to produce said fluorinated alcohol.

2. A process for producing a fluorinated alcohol in accordance with claim 1, wherein said hydrofluorocarbon has a general formula:

[F(CF$_2$)n] CH$_3$, wherein n=1–5.

3. A process for producing a fluorinated alcohol in accordance with claim 1, wherein the fluorinated alcohol has a general formula:

[F(CF$_2$)n] CH$_2$OH, wherein n=1–5.

4. A process for producing a fluorinated alcohol in accordance with claim 1, wherein said oxidizing agent is selected from the group consisting of air, molecular oxygen and mixtures of nitrogen and oxygen.

5. A process for producing a fluorinated alcohol in accordance with claim 1, wherein the oxidizing agent is air.

6. A process for producing a fluorinated alcohol in accordance with claim 1, wherein said process is performed in a reactor packed with a particulate phase selected from alumina and copper metal turnings.

luorocarbon is 1,1,1-trifluoroethane and said fluorinated alcohol is 2,2,2-trifluoroethanol.

15. A process for producing a fluorinated alcohol in accordance with claim 14, wherein a molar ratio of said fluorine to said 1,1,1-trifluoroethane is from 0.1 to 0.5.

16. A process for producing a fluorinated alcohol in accordance with claim 14, wherein a molar ratio of said air to said 1,1,1-trifluoroethane is from 2.0 to 10.0.

17. A process for producing a fluorinated alcohol in accordance with claim 14, wherein said process takes place in a fluidized bed reactor.

18. A process for producing a fluorinated alcohol in accordance with claim 14, wherein said process takes place at a temperature ranging from 150° C. to 250° C. with a residence time of 2 to 100 seconds.

19. A vapor phase process for producing 2,2,2-trifluoroethanol, comprising reacting 1,1,1-trifluoroethane with fluorine and air in a fluidized bed reactor, wherein a molar ratio of fluorine to 1,1,1-trifluoroethane is from 0.1 to 0.5, a molar ratio of air to 1,1,1-trifluoroethane is from 2.0 to 10.0, a temperature in said fluidized bed reactor ranges from 175° C. to 225° C., a residence time ranges from 30 to 60 seconds, to produce said 2,2,2-trifluoroethanol.

* * * * *